(12) United States Patent
Barrett et al.

(10) Patent No.: US 9,320,701 B2
(45) Date of Patent: Apr. 26, 2016

(54) SUN-CARE COMPOSITIONS

(75) Inventors: Christine M. Barrett, Oakland, NJ (US); Tracey Ross, Hewitt, NJ (US); RitaMarie Guerrero, Hillsborough, NJ (US); David K. Hood, Basking Ridge, NJ (US); Hani Fares, Somerset, NJ (US)

(73) Assignee: ISP INVESTMENTS INC., Wilmington, DE (US)

( * ) Notice: Subject to any disclaimer, the term of this patent is extended or adjusted under 35 U.S.C. 154(b) by 0 days.

(21) Appl. No.: 13/388,688

(22) PCT Filed: Aug. 5, 2010

(86) PCT No.: PCT/US2010/044500
§ 371 (c)(1),
(2), (4) Date: May 4, 2012

(87) PCT Pub. No.: WO2011/017491
PCT Pub. Date: Feb. 10, 2011

(65) Prior Publication Data
US 2012/0219515 A1    Aug. 30, 2012

(51) Int. Cl.
*A61K 8/00* (2006.01)
*A61K 8/18* (2006.01)
*A61Q 17/04* (2006.01)
*A61K 8/81* (2006.01)

(52) U.S. Cl.
CPC ............... *A61K 8/8182* (2013.01); *A61K 8/817* (2013.01); *A61Q 17/04* (2013.01)

(58) Field of Classification Search
CPC .................................................... A61K 8/8182
See application file for complete search history.

(56) References Cited

U.S. PATENT DOCUMENTS

| 4,524,061 | A | * | 6/1985 | Cho et al. .................. 424/60 |
| 5,641,480 | A | * | 6/1997 | Vermeer ................ 424/70.24 |
| 5,916,541 | A | | 6/1999 | Stewart |
| 6,284,227 | B1 | | 9/2001 | Stewart |
| 6,436,376 | B1 | | 8/2002 | Hansenne et al. |
| 6,436,377 | B1 | | 8/2002 | Hansenne et al. |
| 7,368,105 | B2 | | 5/2008 | Candau |
| 7,416,719 | B2 | | 8/2008 | Huerta et al. |
| 2005/0079141 | A1 | | 4/2005 | Zander et al. |
| 2005/0186160 | A1 | | 8/2005 | Aust et al. |
| 2006/0013839 | A1 | | 1/2006 | Yu |
| 2006/0110346 | A1 | | 5/2006 | Lu |
| 2006/0233726 | A1 | * | 10/2006 | Nia .............................. 424/59 |
| 2008/0317795 | A1 | | 12/2008 | Traynor et al. |

OTHER PUBLICATIONS

PCT, International Search Report, International Application No. PCT/US2010/044500 (mailed Sep. 17, 2010, published Feb. 10, 2011).

* cited by examiner

*Primary Examiner* — Paul Dickinson
(74) *Attorney, Agent, or Firm* — Thompson Hine LLP; William J. Davis

(57) ABSTRACT

A sun-care composition having an SPF value of at least (15) containing (a) one or more sun-care actives; (b) a copolymer (or a terpolymer) containing (A) at least one vinyl pyrrolidone monomer and (i) at least one vinyl caprolactam monomer or (ii) at least one vinyl acetate monomer or (B) at least one vinyl caprolactam monomer and at least one vinyl acetate monomer; and (c) a pharmaceutically/cosmetically/dermatologically acceptable vehicle.

11 Claims, No Drawings

SUN-CARE COMPOSITIONS

CROSS REFERENCE TO RELATED APPLICATION

This application claims the benefit of U.S. Provisional Application Ser. No. 61/231,855 filed Aug. 6, 2009, the entire contents of which are hereby incorporated by reference.

BACKGROUND

The present application relates to a sun-care composition having an SPF value of at least 15 comprising: (a) one or more sun-care actives; (b) a copolymer (or a terpolymer) containing (A) at least one vinyl pyrrolidone monomer and at least one vinyl caprolactam monomer or at least one vinyl acetate monomer or (B) at least one vinyl caprolactam monomer and at least one vinyl acetate monomer; and (c) a cosmetically/dermatologically acceptable vehicle. The sun-care actives include UV-A and/or UV-B sunscreens or mixtures thereof.

More particularly, the present application relates to sunscreen compositions that provide a boost in the SPF value of the composition and provide enhanced sensory properties when applied. Thus, the present application describes compositions that provide efficient photo protection and that can be applied in a smooth, continuous film over the skin which leaves the skin feeling soft and silky.

UV radiation is part of the electromagnetic (light) spectrum that reaches the earth from the sun. It has wavelengths shorter than visible light, making it invisible to the naked eye. These wavelengths are classified as UVA, UVB, or UVC, with UVA the longest of the three at 320-400 nanometers (nm, or billionths of a meter). UVB ranges from 290 to 320 nm. With even shorter rays, most UVC is absorbed by the ozone layer and does not reach the earth.

Sunlight or ultraviolet radiation in the UV-B range is known to be the primary cause of sunburn whereas UV-A radiation, which makes up 90% of solar radiation produces tanning of the skin. However, in that process, UV-A rays cause, in particular, a loss in the elasticity of the skin and the appearance of wrinkles, promoting a premature aging thereof.

Besides the immediate malady of sunburn, excessive sunlight exposure can lead to skin disorders. For instance, prolonged and constant exposure to the sun may lead to actinic keratoses and carcinomas. Another long-term effect is premature aging of the skin. This condition is characterized by skin that is wrinkled, cracked and has lost its elasticity.

Sunscreen compositions are applied to the skin to protect the skin from the sun's ultraviolet rays. Over the past 10 years, awareness of the detrimental effects of unprotected UV exposure has increased and, as a result, consumers are seeking higher levels of protection. Further the standards of the sunscreens have been raised by stringent testing requirements by Regulatory authorities. The most significant changes within these regulations are the new requirements for UVA protection and the added test for photostability of finished sunscreen formulations. The majority of sun-care products currently require SPF levels of at least 30, reaching upwards of 50+. As a result, high levels of UVA protection are required in order to make a UVA claim.

As the sun-are market is becoming more competitive, companies are separating themselves from competitors by launching higher SPF products and thus claiming higher UV protection. To achieve protection across a wide range, sunscreen makers may include several different sunscreen ingredients. One of the most opted way of achieving higher SPF values, is to increase the amount of sunscreens in the product. This approach however will increase the cost of the product and might negatively impact the sensory characteristics of the product. Others have added small amounts of UV absorbers like butyl octyl salicylate as boosters to formulations. Others increased SPF by adding light scattering/refracting polymers to the product such as styrene/acrylates copolymers.

Among the most desirable options is finding a number of absorbers that work in synergy or by using various polymers that provide a continuous film on the skin. A wide variety of cosmetic/dermatological compositions intended for the enhanced performance of sunscreens of human skin is known in the art.

U.S. Pat. No. 6,436,376 discloses a regime/regimen for improved UV-photoprotecting human skin, hair and/or scalp against the deleterious effects of ultraviolet irradiation, comprising topically applying thereon (a) an effective UV-photoprotecting amount of at least one UV-A and/or UV-B sunscreen and (b) an amount of the copolymer tricontanyl PVP (Ganex-WP-660). The compositions are said to be particularly effective for the sunscreen avobenzone.

Similarly, U.S. Pat. No. 6,436,377 claims a regime/regimen for improved UV-photoprotecting human skin, hair and/or scalp against the deleterious effects of ultraviolet irradiation, comprising applying thereon at least one UV-A and/or UV-B sunscreen and the interpolymer PVP/dimethiconylacrylate/polycarbamyl/polyglycol ester in an amount effective to significantly enhance the SPF value.

U.S. Pat. No. 7,368,105 discloses photoprotective compositions comprising at least one dibenzoylmethane UV-screening agent, a stabilizing admixture comprising arylalkyl benzoate compound and at least one bis-resorcinyl triazine compound.

U.S. Pat. No. 4,524,061 discloses polymeric sunscreen agents comprising interpolymers of (a) an olefinic p-aminobenzoate devoid of hydroxy substitution; (b) N-vinylpyrrolidone; (c) a monomer selected from the group consisting of a vinyl lactam having a number average molecular weight of at least 125, an acrylate or methacrylate or any mixture thereof and optionally (d) acrylic or methacrylic acid.

Further, U.S. Pat. No. 5,916,541 discloses a waterproof sunscreen and insect repellent stable emulsion composition comprising an emulsifying agent for forming a stable emulsion; and a film forming agent present in an amount effective to form a thin film when the composition is applied to the skin of a person and provides SPF factors of about 2 to about 50. Poly (vinyl pyrrolidone/1-triacontene) is specifically disclosed.

A consumer consideration while purchasing a sunscreen product is how the product feels and how well it spreads over the skin. Typically, consumers want a sunscreen that feels soft and silky and can be applied in a smooth, continuous film over the skin. Ultimately, product feel could determine whether the consumer decides to purchase the product.

U.S. Pat. No. 7,416,719 describes a sunscreen composition comprising: (a) at least one sunscreen agent; and (b) at least one lauryl glucoside emulsifier, wherein the lauryl glucoside emulsifier imparts an enhanced soft, silky feel to the composition.

With such an advancement and awareness among the consumer, it is always and foremost desired to have sunscreens formulated with the goal of inhibiting skin damage from the sun's rays. The sunscreen composition filters or blocks the harmful UV-A and UV-B rays that can damage and harm the skin. Thus, the present application discloses sun-care compositions with enhanced performance and aesthetics.

SUMMARY

The present application discloses sun-care compositions comprising one or more sun-care actives in combination with specific polymers derived from vinyl lactams. In accordance with certain embodiments, the compositions exhibit enhanced/elevated efficiency of the sunscreen active. The compositions of the invention provide the user with an enhanced soft, silky feel when applied to skin while still providing superior protection from damaging ultraviolet light.

In accordance with certain aspects of the present invention, there is provided a sun-care composition comprising one or more sun-care actives in combination with specific polymers derived from vinyl lactams which are capable of enhancing/elevating the efficiency of the sunscreen.

In accordance with particular aspects, the present application discloses sun-care composition having an SPF value of at least 15 comprising:
(a) one or more sun-care actives;
(b) a copolymer (or a terpolymer) containing the residue of (A) at least one vinyl pyrrolidone monomer and (i) at least one vinyl caprolactam monomer or (ii) at least one vinyl acetate monomer or (B) at least one vinyl caprolactam monomer and at least one vinyl acetate monomer; and
(c) a pharmaceutically/cosmetically/dermatologically acceptable vehicle.

The sun-care active can be selected from the group consisting of UV-A sunscreens, UV-B sunscreens, physical sun blockers and combinations thereof. The sun-care composition of the present invention typically has an SPF of at least 15, more particularly about 25, and in certain cases from about 50 to about 130.

In a particular embodiment, the copolymer (or a terpolymer) containing at least one vinyl pyrrolidone monomer and at least one vinyl caprolactam monomer can be selected from the group consisting of vinyl pyrrolidone/vinyl caprolactam/ dimethylaminoethylmethacrylate (DMAEMA) (available from ISP under the brand name of Advantage® S, Advantage® HC-37, Advantage® LC-E), vinyl pyrrolidone/vinyl caprolactam/dimethylaminopropylmethylacrylamide (DMAPMA) acrylate (available from ISP under the brand name of Aquaflex® SF-40), vinyl pyrrolidone/vinyl caprolactam/dimethylaminopropylmethylacrylamide acrylate/methacryloylaminopropyl lauryldimoniumchloride (available from ISP under the brand name of Aquastyle® 300) and vinyl pyrrolidone/vinyl caprolactam (available from BASF under the brand name Luvitec55K, 65W).

In another embodiment of the present invention the copolymer containing at least one vinyl pyrrolidone monomer or at least one vinyl caprolactam monomer and at least one vinyl acetate monomer contains units derived from vinyl pyrrolidone and vinyl acetate present in a ratio from about 70:30 to about 30:70 (available from ISP under various brands PVP/VA-S-630, PVP/VA-735, PVP/VA-635, PVP/VA-535, PVP/VA-335).

The one or more sun-care actives can be used in an amount from about 1 wt. % to about 50 wt. % of the total weight of the composition. The copolymer (or terpolymer) may be used from about 0.05 wt. % to about 10 wt. % of the total weight of the composition, more preferably, from about 0.5 wt. % to about 2 wt. % of the total weight of the composition.

The pharmaceutically/cosmetically/dermatologically acceptable vehicle is well known to those skilled in the art and includes a cream, a lotion, an emulsion, an oil, a spray, a gel, a aerosol, an aqueous or hydra-alcoholic solution, a suspension, an anhydrous solution, a serum, an ointment, a gel, or a paste.

The sun-care composition of the present invention can further comprise one or more additional components selected from the group consisting of skin-feel additives, moisturizing agents, film former/waterproofing agents, pH adjuster/chelating agents, emulsifiers, preservatives, anti-aging agents, skin whitening agents, exfoliating agents, treatment ingredients, fragrances and mixtures thereof.

The sun-care composition in a preferred embodiment is in the form of an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous gel, an aqueous gel, an alcoholic solutions or a hydro-alcoholic solution.

This invention also provides a method for enhancing the SPF-value of one or more sun-care actives in UV-photoprotecting sun-care compositions comprising admixing and intimately formulating the pharmaceutically/cosmetically/dermatologically acceptable carrier and a copolymer or terpolymer comprising (A) at least one vinyl pyrrolidone monomer and (i) at least one vinyl caprolactam monomer or (ii) at least one vinyl acetate monomer or (B) at least one vinyl caprolactam monomer and at least one vinyl acetate monomer in an amount effective to enhance the SPF value of said one or more sun-care actives.

DETAILED DESCRIPTION

The present invention relates to a SPF enhanced sun-care composition comprising one or more sun-care actives, a copolymer (or a terpolymer) and a pharmaceutically/cosmetically/dermatologically acceptable vehicle. The copolymer (or a terpolymer) comprises (A) at least one vinyl pyrrolidone monomer and (i) at least one vinyl caprolactam monomer or (ii) at least one vinyl acetate monomer or (B) at least one vinyl caprolactam monomer and at least one vinyl acetate monomer.

While applicants do not wish to be bound by any theories, it is believed that the mechanism of enhancement of SPF is generally attributed to the ability of the polymer to make a uniform film of the product onto the skin. The distribution of the sunscreen actives in the film is considered key to the boosting the effect of such polymer. In addition, the uniformity of the film is also of great importance. Since the surface of the skin is really not very uniform, many polymers do not have the ability of forming continuous films on the skin. That is why not all film formers are considered SPF boosters. The ability to identify such classes of polymers is of key value to formulation chemists as it allows them to achieve higher SPF values with less sunscreen in their formulations. Thus, spreadability, dispersability, uniformity, solubility and compatibility of the selective film polymers as described in the present invention are factors that can lead to the elevated SPF of the sunscreens desired by the present day customers.

The sunscreen composition of the present invention is uniquely formulated to provide an elevated SPF and enhanced feeling of softness and silkiness when the sunscreen composition is applied to the skin. Moreover, the composition is capable of being easily and uniformly applied over the skin. These enhanced properties are achieved, in large part, by formulating the sunscreen composition as described herein.

According to the present invention, the one or more suncare actives may be selected from the group consisting of UV-A sunscreens, UV-B sunscreens, physical sun blockers and combinations thereof.

Examples of various UV-A or UV-B sunscreens include p-aminobenzoic acid and its derivatives, anthranilates, benzophenones, camphor derivatives, cinnamic derivatives, dibenzoyl methanes, beta,beta-diphenylacrylate derivatives, salicylic derivatives, triazine derivatives, benzimidazole compounds, bis-benzoazolyl derivatives, methylene bis-(hydroxyphenylbenzotriazole) compounds, sunscreen polymers, silicones, and mixtures thereof.

Examples of physical sun blockers include cerium oxides, chromium oxides, cobalt oxides, iron oxides, red petrolatum, silicone-treated titanium dioxides, titanium dioxides, zinc oxides, and/or zirconium oxides and mixtures thereof.

In a certain embodiment, the sun-care active can be selected from the group consisting of p-aminobenzoic acid, oxyethylene (25 mol) p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammunium)-benzyliden-bornan-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4, 4'dimethoxybenzophenone, 2-hydroxy-4-n-octoxybenzophenone, 2-hydroxy-4-methoxy-4'-methoxybenzophenone, .beta.(2-oxoborn-3-ylidene)-tolyl-4-sulfonic acid and soluble salts thereof, 3-(4'-sulfo) benzyliden-bornan-2-one and soluble salts thereof, 3-(4'methylbenzylidene)-d,1-camphor, 3-benzylidene-d,1-camphor, benzene 1,4-di(3-methylidene-10-camphosulfonic) acid, urocanic acid, 2,4,6-tris[p-(2'-ethylhexyl-1'-oxycarbonyl)-anilino]-1,3,5-triazine, 2-[(p-(tertiobutylamido) anilino]-4,6-bis-[(p-(2'-ethylhexyl-1'-oxycarbonyl)anilino]-1,3,5-triazine, 2,4-bis{[4-(2-ethyl-hexyloxy)]-2-hydroxy]-phenyl}-6-(4-methoxyphenyl)-1,3,5-triazine, N-(2 et 4)-[(2-oxoborn-3-yliden)methyl]benzyl]-acrylamide, 1,4-bisbenzimidazolyl-phenylen-3,3',5,5'-tetrasulfonic acid, the benzalmalonate-substituted polyorganosiloxanes, the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol], solubilized 2,2'-methylene-bis-[6-(2H-benzotriazol-2-yl)-4-(methyl) phenol, cerium oxides, chromium oxides, cobalt oxides, iron oxides, red petrolatum, silicone-treated titanium dioxide, titanium dioxides, zinc oxides, and/or zirconium oxides and acid, salts, esters, derivatives and any combinations thereof.

The amount of sun-care active employed will depend on the level of protection desired. Although not to be construed as limiting, compositions will typically contain sun-care active in the range of about 1 wt. % to about 50 wt. % of the total weight of the composition. The amount of sunscreen agent in the composition will vary in the above range depending on the sun protection factor (SPF) desired. The higher the SPF, the greater the total amount of sunscreen agent used. In accordance with certain embodiments, the composition contains more than one sunscreen agent.

The term "SPF number" used in connection with the present invention refers to the dose required to produce a minimal erythema on protected skin, divided by the dose required to produce the same degree of skin erythema without the product applied.

$$SPF = \frac{\text{minimal erythema dose (MED) on protected skin}}{MED \text{ on unprotected skin}}$$

The sun-care composition of the present invention should provide an SPF value of at least 15. More particularly, it should provide an SPF of at least 25 and in another particular embodiment of the invention provides an SPF of from about 50 to about 130.

The term copolymer (or a terpolymer) used in connection with the present invention refers to polymers/copolymers/terpolymers of vinyl pyrrolidones, capable of enhancing the SPF value to at least 15 and more particularly from about 50 to about 130 and also forming a uniform smooth continuous film over the skin surface to provide complete protection.

In a particular embodiment, the copolymer (or a terpolymer) comprising at least one vinyl pyrrolidone monomer and at least one vinyl caprolactam monomer is selected from the group consisting of vinyl pyrrolidone/vinyl caprolactam/dimethylaminoethylmethacrylate (DMAEMA) (available from ISP under the brand name of Advantage® S, Advantage® HC-37, Advantage® LC-E), vinyl pyrrolidone/vinyl caprolactam/dimethylaminopropylmethylacrylamide (DMAPMA) (available from ISP under the brand name of Aquaflex® SF-40), vinyl pyrrolidone/vinyl caprolactam/dimethylaminopropylmethylacrylamide(DMAPA)/methacryloylaminopropyl lauryldimoniumchloride (available from ISP under the brand name of Aquastyle® 300).

In one particular embodiment, the copolymer (or a terpolymer) comprises at least one vinyl pyrrolidone monomer and at least one vinyl acetate monomer present in a weight ratio from about 70:30 to about 30:70 (available from ISP under various brands such as PVP/VA-S-630, PVP/VA-735, PVP/VA-635, PVP/VA-535, PVP/VA-335). Molecular weights for some specific examples are provided below:

| Polymer | Typical Molecular Weight |
| --- | --- |
| E335 | 28,800 |
| E535 | 36,700 |
| E635 | 38,200 |
| E735 | 56,700 |
| I335 | 12,700 |
| I535 | 19,500 |
| I735 | 22,300 |

In another embodiment, the copolymer or terpolymer comprises at least one vinyl caprolactam monomer and at least one vinyl acetate monomer.

The amount of copolymer (or terpolymer) in the present invention typically ranges from about 0.05 wt. % to about 10 wt. % of the total weight of the composition. More particularly it may range from about 0.5 wt. % to about 2 wt. % of the total weight of the composition.

While the molecular weight of the polymer is not believed to be critical to the practice of this invention, good results have been achieved using polymers having a molecular weight from about 5,000 to 100,000, and more particularly from about 10,000-65,000. Molecular weight in g/mol may be based on weight average molecular weight determined by methods, such as light scattering, known to those of ordinary skill in the art.

Examples of pharmaceutically/cosmetically/dermatologically acceptable vehicles include a cream, a lotion, an emulsion, an oil, a spray, a gel, a aerosol, an aqueous or hydra-alcoholic solution, a suspension, an anhydrous solution, a powder, a serum, an ointment, a gel, or a paste.

The amount of cosmetically acceptable vehicle in the present composition will vary considerably based upon product form, but typically will range from about 30 wt % to about 99.95 wt % and preferably about 50 wt % to about 99 wt %, based upon the total weight of the composition.

In a particular embodiment, the sun-care composition further comprises one or more additional components selected from the group consisting of skin-feel additives, moisturizing agents film former/waterproofing agents, pH adjuster/chelating agents, emulsifiers, preservatives, anti-aging agents, skin whitening agents, exfoliating agents, treatment ingredients, fragrances and mixtures thereof.

The composition can be made into any suitable product form. Such product forms include, but are not limited to, an aerosol, balm, cream, gel, lotion, mousse, patch, pomade, pump spray, roll-on, solution, stick or towelette.

In a particular embodiment, the present composition may be formulated in the form of an emulsion. The emulsion may be, for example, anhydrous, an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous gel, an aqueous gel, an alcoholic solutions or a hydro-alcoholic solution.

The sunscreen compositions may be prepared by using techniques and methods well known in the art. In general, ingredients are incorporated by mixing and applying heat if necessary, until the composition is uniform and homogeneous. The composition may be homogenized to ensure homogeneity and to build the proper viscosity. The sunscreen compositions of the present invention typically are then packaged in any package or container suitable for a sunscreen composition.

In another particular embodiment of the present invention, there is provided a method for enhancing the SPF-value of one or more sun-care actives in UV-photoprotecting sun-care compositions comprising admixing and intimately formulating the pharmaceutically/cosmetically/dermatologically acceptable carrier and a copolymer (terpolymer) comprising at least (A) one vinyl pyrrolidone monomer and (i) at least one vinyl caprolactam monomer or (ii) at least one vinyl acetate monomer in an amount effective to enhance the SPF value of said one or more sun-care actives or (B) at least one vinyl caprolactam monomer and at least one vinyl acetate monomer.

The sunscreen composition of the present invention is uniquely formulated to provide an enhanced feeling of softness and silkiness when the sunscreen composition is applied to the skin. Moreover, the composition is capable of being easily and uniformly applied over the skin.

The following examples further illustrate the invention.

|  | INCI Name | | | | | | | | | |
|---|---|---|---|---|---|---|---|---|---|---|
|  | 77-1 A | 79-4 B | 141-1 C | 77-2 D | 145-2 E | 145-4 F | 148-7 G | 148-6 H | 145-5 I | 145-6 J |
| Avobenzone | 2.0 | 2.0 | 2.0 | 3.0 | 3.00 | 3.00 | 2.0 | 2.0 | 2.0 | 2.0 |
| Homosalate | 7.0 | 7.0 | 7.0 | 8.0 | 8.00 | 8.00 | 7.0 | 7.0 | 7.0 | 7.0 |
| Octisalate | 5.0 | 5.0 | 5.0 | 4.0 | 4.00 | 4.00 | 5.0 | 5.0 | 5.0 | 5.0 |
| Octinoxate | 7.5 | 7.5 | 7.5 |  |  |  | 7.5 | 7.5 | 7.5 | 7.5 |
| Benzophenone-3 | 3.0 | 3.0 | 3.0 | 5.0 | 5.00 | 5.00 | 3.00 | 3.0 | 3.0 | 3.0 |
| Octocrylene |  |  |  | 2.35 | 2.35 | 2.35 |  |  |  |  |
| Aquaflex SF-40 |  |  |  |  |  |  |  | 1.5 | 0.5 | 1.5 |
| Advantage S |  |  |  |  |  |  | 0.5 |  | 0.5 | 0.5 |
| PVP/VA E535 |  | 1.0 |  |  |  |  |  |  |  |  |
| PVP/VA S630 |  |  | 1.0 |  |  | 1.00 |  |  |  |  |
| PVP/VA E735 |  |  |  |  | 1.00 |  |  |  |  |  |
| Ethanol | QS | QS | QS | QS | QS | QS | QS | QS | QS | QS |
| Percent Boost | N/A | 43.16 | 74.9 | N/A | 24.05 | 30.84 | 45.67 | 26.34 | 57.18 | 47.5 |

|  | INCI Name | | | | | | |
|---|---|---|---|---|---|---|---|
|  | 60-2 K | 60-1 L | 95-2 M | 10-2 N | 141-2 O | 95-1 P | 142-4 Q |
| Phase A |  |  |  |  |  |  |  |
| Deionized water | QS | QS | QS | QS | QS | QS | QS |
| Disodium EDTA | 0.10 | 0.10 | 0.10 | 0.10 | 0.10 | 0.10 | 0.10 |
| Glycerin | 2.00 | 2.00 | 2.00 | 2.00 | 2.00 | 2.00 | 2.00 |
| Acrylates/C10-30 alkyl acrylate crosspolymer | 0.30 | 0.30 | 0.30 | 0.30 | 0.30 | 0.30 | 0.30 |
| Phase B |  |  |  |  |  |  |  |
| Sodium lauryl lactylate (and) Cetearyl alcohol (and) glyceryl Stearate | 1.25 | 1.25 | 1.25 | 1.25 | 1.25 | 1.25 | 1.25 |
| Behenyl alcohol | 0.50 | 0.50 | 0.50 | 0.50 | 0.50 | 0.5 | 0.50 |
| Ceteareth 20 | 3.50 | 3.50 | 3.50 | 3.50 | 3.50 | 3.50 | 3.50 |
| Diisopropyl adipate | 6.00 | 6.00 | 6.00 | 6.00 | 6.00 | 6.00 | 6.00 |
| Avobenzone | 3.00 | 2.00 | 2.00 | 3.00 | 2.00 | 2.00 | 3.00 |
| Homosalate | 8.00 | 7.00 | 7.00 | 8.00 | 7.00 | 7.00 | 8.00 |
| Octisalate | 4.00 | 5.00 | 5.00 | 4.00 | 5.00 | 5.00 | 4.00 |

| -continued | | | | | | | |
|---|---|---|---|---|---|---|---|
| Octinoxate | | 7.50 | 7.50 | | 7.50 | 7.50 | |
| Benzophenone-3 | 5.00 | 3.00 | 3.00 | 5.00 | 3.00 | 3.00 | 5.00 |
| Octocrylene | 2.35 | | | 2.35 | | | 2.35 |
| Aquaflex SF-40 | | | | | 0.50 | 1.50 | 0.50 |
| Advantage S | | | | | 0.50 | 0.50 | 0.50 |
| PVP/VA E535 | | | | | | | |
| PVP/VA S630 | | | 1.00 | | | | |
| PVP/VA E735 | | | | 1.00 | | | |
| Phase C | | | | | | | |
| Triethanolamine | 0.32 | 0.32 | 0.32 | 0.32 | 0.32 | 0.32 | 0.32 |
| Propylene glycol (and) diazolidinyl urea (and) methylparaben (and) propylparaben | 1.00 | 1.00 | 1.00 | 1.00 | 1.00 | 1.00 | 1.00 |
| Percent Boost | N/A | N/A | 24.66 | 25.51 | 34.11 | 39.70 | 43.49 |

The invention has been described in detail with particular reference to particular embodiments thereof, but it will be understood that variations and modifications can be effected within the spirit and scope of the invention.

What is claimed is:

1. A sun-care composition having an SPF value of at least 15 comprising an admixture of:
   (a) one or more sun-care actives;
   (b) a copolymer (or a terpolymer) containing at least one vinyl pyrrolidone monomer and at least one vinyl caprolactam monomer; and
   (c) a pharmaceutically/cosmetically/dermatologically acceptable vehicle.

2. The composition according to claim 1, wherein the sun-care active is selected from the group consisting of UV-A sunscreens, UV-B sunscreens, physical sun blockers and combination thereof.

3. The composition according to claim 1, wherein the sun-care active is selected from the group consisting of p-aminobenzoic acid, oxyethylene (25 mol) p-aminobenzoate, 2-ethylhexyl p-dimethylaminobenzoate, ethyl N-oxypropylene p-aminobenzoate, glycerol p-aminobenzoate, 4-isopropylbenzyl salicylate, 2-ethylhexyl 4-methoxycinnamate, methyl diisopropylcinnamate, isoamyl 4-methoxycinnamate, diethanolamine 4-methoxycinnamate, 3-(4'-trimethylammunium)-benzyliden-bornan-2-one methylsulfate, 2-hydroxy-4-methoxybenzophenone, 2-hydroxy-4-methoxybenzophenone-5-sulfonate, 2,4-dihydroxybenzophenone, 2,2',4,4'-tetrahydroxybenzophenone, 2,2'-dihydroxy-4,4' dimethoxybenzophenone, 2-hydroxy-4-n-octoxybenzophenone, 2-hydroxy-4-methoxy-4'-methoxybenzophenone, .beta.(2-oxoborn-3-ylidene)-tolyl-4-sulfonic acid and soluble salts thereof, 3-(4'-sulfo)benzyliden-bornan-2-one and soluble salts thereof, 3-(4'methylbenzylidene)-d,1-camphor, 3-benzylidene-d,1-camphor, benzene 1,4-di(3-methylidene-10-camphosulfonic) acid, urocanic acid, 2,4,6-tris[p-(2'-ethylhexyl-1'-oxycarbonyl)-anilino]-1,3,5-triazine, 2-[(p-(tertiobutylamido)anilino]-4,6-bis-[(p-(2'-ethylhexyl-1'-oxycarbony-1) anilino]-1,3,5-triazine, 2,4-bis {[4-(2-ethyl-hexyloxy)]-2-hydroxy]-phenyl}-6-(4-methoxyphenyl)-1,3-,5-triazine, N-(2 et 4)-[(2-oxoborn-3-yliden)methyl] benzyl]-acrylamide, 1,4-bisbenzimidazolyl-phenylen-3,3',5,5'-tetrasulfonic acid, the benzalmalonate-substituted polyorganosiloxanes, the benzotriazole-substituted polyorganosiloxanes (Drometrizole Trisiloxane), dispersed 2,2'-methylene-bis-[6-(2H-benzotriazol-2-yl)-4-(1,1,3,3-tetramethylbutyl)phenol], solubilized 2,2'-methylene-bis-[6-(2H-benzotriazol-2-yl)-4-(methyl)phenol], cerium oxides, chromium oxides, cobalt oxides, iron oxides, red petrolatum, silicone-treated titanium dioxide, titanium dioxide, zinc oxide, and zirconium oxide and acid, salts, esters, derivatives and combinations thereof.

4. The composition according to claim 1, having an SPF of at least 25.

5. The composition according to claim 1, wherein said one or more sun-care actives are present in an amount of about 1 wt. % to about 50 wt. % of the total weight of the composition.

6. The composition according to claim 1, wherein said copolymer (or terpolymer) is about 0.05 wt. % to about 10 wt. % of the total weight of the composition.

7. The composition according to claim 6, wherein said copolymer (or terpolymer) is about 0.5 wt. % to about 2 wt. % of the total weight of the composition.

8. The composition according to claim 1, wherein said pharmaceutically/cosmetically/dermatologically acceptable vehicle is selected from the group consisting of a cream, a lotion, an emulsion, an oil, a spray, a gel, an aerosol, an aqueous solution, a hydra-alcoholic solution, a suspension, an anhydrous solution, a powder, a serum, an ointment, a gel, a paste and combinations thereof.

9. The composition according to claim 1, further comprising one or more additional components selected from the group consisting of skin-feel additives, moisturizing agents film former/waterproofing agents, pH adjuster/chelating agents, emulsifiers, preservatives, and mixtures thereof.

10. The sun-care composition according to claim 1 in the form of an oil-in-water emulsion, a water-in-oil emulsion, an oil-water-oil emulsion, a water-oil-water emulsion, a water-in-silicone emulsion, an oily solution, a lipid fusion, a hydro-alcoholic gel, an anhydrous gel, an aqueous gel, an alcoholic solutions or a hydro-alcoholic solution.

11. A method for enhancing the SPF-value of one or more sun-care actives in UV-photoprotecting sun-care compositions comprising admixing and intimately formulating a pharmaceutically/cosmetically/dermatologically acceptable carrier and a copolymer (or terpolymer) comprising at least one vinyl pyrrolidone monomer and at least one vinyl caprolactam monomer in an amount effective to enhance the SPF value of said one or more sun-care actives.

* * * * *